United States Patent [19]

Smith

[11] 4,327,744
[45] May 4, 1982

[54] APPARATUS FOR THE SELF-COLLECTION OF CERVICAL CELL SPECIMENS

[76] Inventor: Louise W. Smith, 400 Swedesford Rd., Gwynedd Valley, Pa. 19437

[21] Appl. No.: 161,669

[22] Filed: Jun. 23, 1980

[51] Int. Cl.³ .............................................. A61B 17/42
[52] U.S. Cl. .................................. 128/759; 128/749; 128/304; 128/361
[58] Field of Search ............... 128/759, 757, 749, 304, 128/361

[56] References Cited

U.S. PATENT DOCUMENTS

| | | | |
|---|---|---|---|
| 2,514,665 | 7/1950 | Myller | 128/757 |
| 2,847,000 | 8/1958 | Nieburgs . | |
| 2,847,012 | 8/1958 | Eastman | 128/361 |
| 3,017,879 | 1/1962 | Sapit et al. . | |
| 3,592,186 | 7/1971 | Oster | 128/304 X |
| 3,672,351 | 6/1972 | Ubersax et al. | 128/759 X |
| 3,750,646 | 8/1973 | Patterson | 128/759 X |
| 3,838,681 | 10/1974 | Dalton | 128/757 |
| 3,857,384 | 12/1974 | Watson . | |
| 3,867,947 | 2/1975 | Schack | 128/361 |
| 3,995,618 | 12/1976 | Kingsley et al. . | |
| 4,023,559 | 5/1977 | Gaskell . | |
| 4,157,709 | 6/1979 | Schuster et al. . | |

Primary Examiner—Robert W. Michell
Assistant Examiner—Nancy A. B. Swisher
Attorney, Agent, or Firm—Lee, Smith & Jager

[57] ABSTRACT

The apparatus disclosed is for the self-collection of cervical cell specimens for subsequent examination and testing by a medical laboratory, and the apparatus disclosed comprises an elongated tubular finger member formed of a thin elastically resilient material closed at one end and adapted to fit over and resiliently grip the user's finger. Adjacent its closed end the finger member carries a raised resiliently flexible wiping blade. A thin tubular sleeve member, shorter than the finger member and flared at one end, is adapted to accommodate the wiping blade of the finger member, so that the finger member with the sleeve member surrounding the wiping blade thereof may be inserted into the vagina and the wiping blade may then be extended to wipe and thus collect cells from the cervical os. The wiping blade of the finger member then may again be retracted into the sleeve member and the two removed together. The wiping blade of the finger member is thus protected from contaminating contact with the vaginal wall during insertion and removal, as well as, loss of specimen after collection.

8 Claims, 8 Drawing Figures

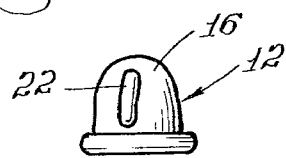
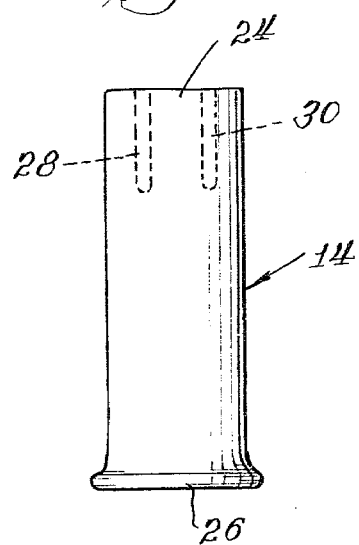
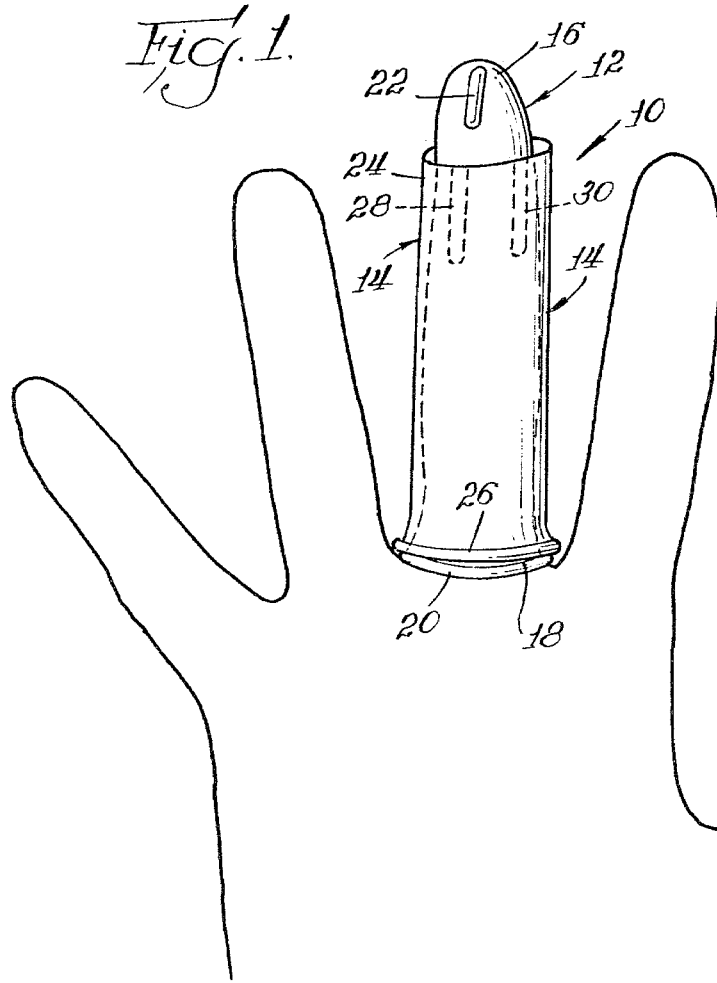
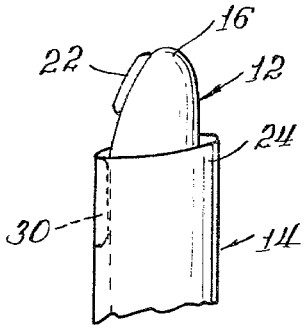

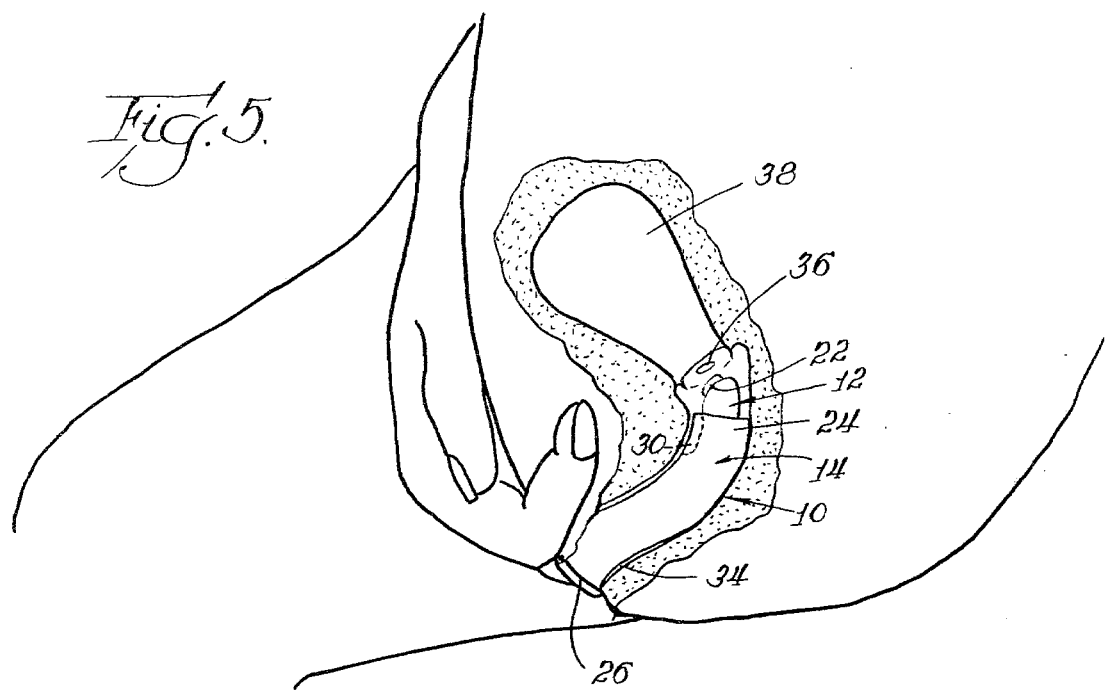
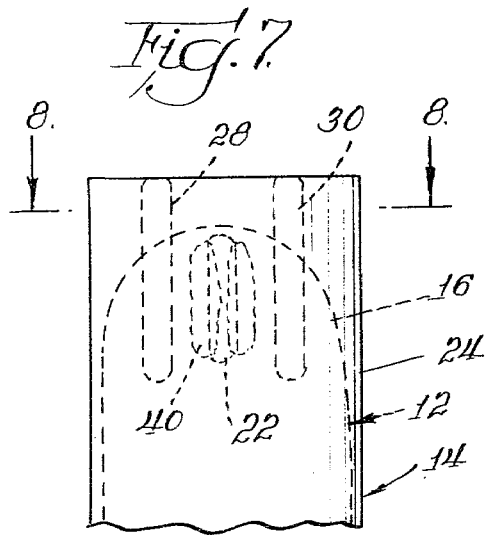
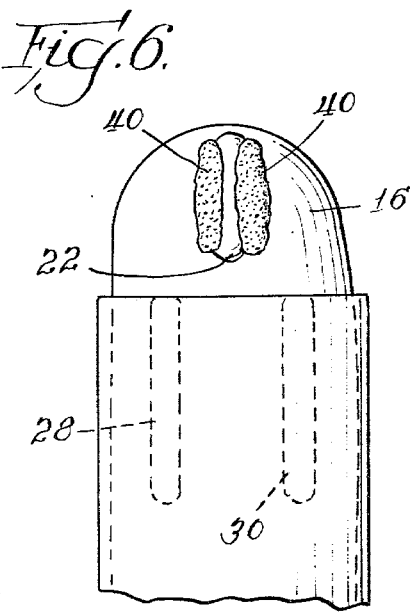
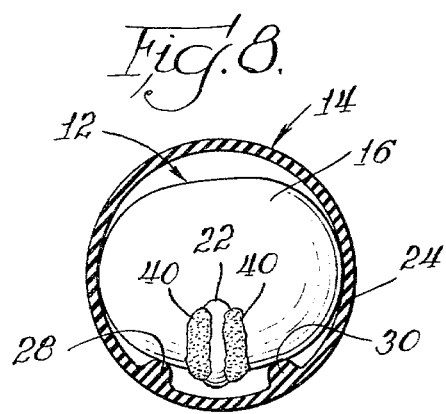

4,327,744

APPARATUS FOR THE SELF-COLLECTION OF CERVICAL CELL SPECIMENS

BACKGROUND OF THE INVENTION

The invention relates to an apparatus for self-collection of cervical cell specimens, and more particularly to an apparatus which an individual can use in the privacy of her own home for the collection of specimen cells from the area of the opening of the uterine cervix for subsequent laboratory testing and microscopic examination.

Because of cost, modesty or self-embarrassment, many women are extremely reluctant to have a physician conduct a routine physical examination in the genital area in order to test for cancer and other diseases. The apparatus of the present invention is intended to overcome this problem by permitting the individual to obtain the specimen cells from the genital area which will permit medical laboratory testing for various diseases of the female genitalia. The apparatus is simple to use and assures that the gathered cell specimens are not "lost" or contaminated in the process.

SUMMARY OF THE INVENTION

In accordance with this invention, an apparatus is provided for insertion into the vagina for the purpose of gathering cervical cell specimens. The apparatus comprises an elongated tubular finger member formed of a thin, elastically resilient material, closed at its distal end and open at its proximate end, and adapted to accommodate and resiliently grip a person's finger. The finger member carries adjacent its distal end a raised wiping or scraping element. A thin, open-ended, tubular sleeve member having an inside dimension larger than the exterior dimension of the finger member is adapted to accommodate therewithin the distal end and wiping element of the finger member. The sleeve member is shorter in length than the finger member, so that it will shield the finger member distal end and wiping element from contaminating contact with the vaginal wall during insertion of the two members into and during withdrawal from the vagina. After insertion of the two members the wiping element at the distal end of the finger member may be extended beyond the distal end of the sleeve member to wipingly engage the cervix and obtain the desired cervical specimens. The wiping element may then be retracted again into the sleeve member prior to withdrawal of the apparatus.

It is preferred that the finger member be constructed of an elastomeric material such as a silicone latex of the type used for surgical gloves. The sleeve member may be constructed of the same material although it is preferred that it be thicker and thus stiffer than the finger member so that it will remain in place as the distal end of the finger member is longitudinally extended and retracted. The sleeve member is preferably flared at its proximate end so that it may be gripped by the thumb of the user, permitting easy insertion and withdrawal of the sleeve and finger members together as a unit.

The raised wiping element on the finger member is preferably an elongated, resiliently flexible, longitudinally extending rib-like blade protruding outwardly from the exterior surface of the finger member, and the sleeve member preferably has a pair of longitudinal ribs which extend inwardly from the interior surface of that member and are spaced apart to accommodate therebetween the longitudinal wiping element blade. The inwardly extending ribs on the sleeve member are of a greater height than the outwardly extending wiping element blade on the finger member so that there will be little or no contact between the interior surface of the sleeve member and the wiping element blade when the distal end of the finger member is retracted within the sleeve member.

BRIEF DESCRIPTION OF THE DRAWINGS

FIG. 1 is a front elevational view of the finger member and sleeve member of an apparatus constructed in accordance with this invention, showing the members after they have been placed on the finger of the user;

FIG. 2 is a front elevational view of the finger member partially rolled preparatory to placement on the user's finger;

FIG. 3 is a front elevational view of the sleeve member of the apparatus;

FIG. 4 is a side elevational view of the distal portions of the finger and sleeve members, with the finger member in its extended position;

FIG. 5 is a perspective view schematically illustrating the manner in which the user may insert the apparatus into the vagina for the self gathering of cervical cell specimens;

FIG. 6 is an enlarged front elevational view of the finger and sleeve members showing the extended finger member after the cell specimens have been collected on the blade thereof;

FIG. 7 is an enlarged front elevational view of the finger and sleeve members showing the finger member retracted into the sleeve member after the specimen cells have been collected on the blade;

FIG. 8 is a sectional view of the apparatus taken substantially along line 8—8 of FIG. 7.

DETAILED DESCRIPTION OF THE PREFERRED EMBODIMENT

The apparatus of the present invention is adapted to be inserted into the vagina of the user for the self-collection of cervical cell specimens to be examined and evaluated by trained technical personnel, such as physicians. The apparatus is particularly adapted for use in the determination of cancer cells in the well-known Pap test, although it may also be used in conjunction with the detection and early treatment of venereal diseases such as gonorrhea.

In FIG. 1 there is illustrated an apparatus 10 constructed in accordance with this invention. The apparatus comprises an elongated tubular finger member 12 and a thin tubular sleeve member 14.

The tubular finger member 12 may be formed of a thin elastically resilient material such as an elastic silicone latex of the type commonly used to form surgical gloves. The finger member is closed at its distal end 16 and open at its proximate end 18, and is adapted to accommodate and resiliently grip the user's finger. Since the finger member is elastic it will accommodate various sizes of finger, although for extremely large and small hands it may be desirable to provide large and small sizes of the finger member. The diameter of the finger member 12 should be small enough to grip the smallest size finger just enough to assure that the member will remain in place on the finger as it is being used.

At the proximate end 18 the finger member may have a resilient thickened band 20 for facilitating the putting on and taking off of the finger member 12 from the finger of the user. This band 20 also facilitates the rolling and unrolling of the finger member.

The finger member 12 should be of a length sufficient to accommodate the user's entire third finger. Since finger length will vary from user to user it is preferred that the finger member be adapted to fit the longest finger. It is particularly advantageous, therefore, if the finger member is partially rolled as illustrated in FIG. 2, so that the user may merely unroll the finger member down over the finger until the rolled portion hits the juncture between the fingers and the palm of the hand as best shown in FIG. 1. Thus the rolled up condition not only facilitates the placement of the member onto the user's finger, but it will also assure that the user's fingertip will extend to the distal end of the finger member 12.

The finger member 12 carries adjacent its distal end 16, a raised wiping element or blade 22 which is integral with and preferably of the same material as the rest of the finger member 12. Preferably the wiping blade 22 is in the form of an elongated longitudinally extending rib-like protrusion from the exterior surface of the finger member 12. The rib-like blade 22, for example, may be on the order of about ⅜ of an inch in length, and between 3/32 and ⅛ of an inch high and about 1/32 of an inch in width. These dimensions will vary, depending upon the precise nature of the elastomeric material. Being made of the same elastomeric material as the rest of the finger member the thicker rib-like blade 22 is rigid enough to retain its rib-like shape but is flexible and resilient so that it can be moved back and forth like a windshield wiper blade to gently wipe cells from the area of the opening of the uterine cervix without injury or irritation.

The tubular sleeve member 14 is also preferably formed of an elastomeric material such as an elastic silicone latex having a wall which is somewhat thicker than the wall of the finger member, thus making it longitudinally stiffer or more firm but still retaining a higher degree of lateral flexibility so that it may readily bend with the finger member 12.

The sleeve member 14 is open at both its distal end 24 and its proximate end 26, and the proximate end 26 is preferably flared to facilitate the holding of the sleeve member by the thumb of the user during insertion and withdrawal of the apparatus from the vagina. The sleeve member 14, for example, may be approximately 2¼ inches long and ⅞ of an inch in diameter. Although it is thicker and therefore, longitudinally stiffer than the finger member 12, it should have the flexibility to stretch laterally to accommodate larger size fingers while permitting longitudinal movement of the finger member 12 relative thereto.

The sleeve member 14 preferably has a pair of ribs 28 and 30 which extend inwardly from the interior surface of the sleeve member, and are spaced apart to accommodate therebetween the raised wiping blade 22 on the distal end of the finger member 12. The ribs 28, for example, may be on the order of ⅜ of an inch long, ⅛ to 5/32 of an inch deep, and approximately ⅛ of an inch wide. It is preferred that such ribs 28 be spaced approximately ⅜ of an inch apart, thus giving plenty of clearance for the thin wiping blade 22 to be moved into and out of the space between these ribs. The ribs are fairly rigid but nevertheless are sufficiently flexible so that this portion of the sleeve can bend with the finger member 12. The inwardly extending ribs 28 and 30 should be a minimum of 1/32 of an inch higher than the height of the wiping blade 22 on the finger member 12 so that the cervical cells which have been scraped onto the sides of the wiping blade will not come into contact with the interior surface of the sleeve member 14, or at least such contact is minimized, thereby protecting the cells from damage and contamination.

It should be pointed out that the ribs 28 and 30 are primarily for protecting the blade 22 and cells 40 from contamination. If the blade 22 is positioned at the very tip of the finger member distal end 16 well inwardly from the remaining side walls of the finger member, it may be sufficiently protected from engagement with the interior wall of the sleeve member 14. In such construction the protection of the ribs may not be needed. However, it is preferred that the blade 22 be located slightly inwardly from the very end at the "ball" of the finger and here protection of the ribs 28 and 30 is highly desirable.

FIG. 5 illustrates the manner in which the apparatus 10 is to be employed by the user for the self-collection of cervical specimens. After the finger member 12 has been rolled down over the third finger of the user's hand, the sleeve member 14 is inserted over the finger member 12 as illustrated in FIG. 1. Before inserting the apparatus into the vagina, the sleeve member 14 is moved upwardly so that the wiping blade 22 on the distal end 16 of the finger member 12 is disposed within the interior of the sleeve member 14 between the ribs 28 and 30 which extend inwardly from the interior surface thereof. This position is best illustrated in FIG. 7. With the finger member 12 and the sleeve member 14 held in this position relative to one another, the apparatus is inserted into the user's vagina 34 in the manner illustrated in FIG. 5. The apparatus is fully inserted until just the flared proximate end 26 of the sleeve member protrudes therefrom. Then the distal end 16 of the finger member 12 is extended beyond the distal end 24 of the sleeve member 14, and the wiping blade 22 is brought into contact with the external os 36 forming the opening to the uterus 38. The wiping blade 22 is then moved back and forth like a windshield wiping blade to wipe or gently scrape cells from the area of the cervical os. The cervical cells 40 will accumulate at the sides of the wiping blade 22, as best illustrated in FIGS. 6–8.

After the gentle wiping or scraping action has been completed and the cervical cell specimens 40 have been accumulated on and at the sides of the flexible wiping blade 22, the user may hold the sleeve member 14 in place with the free hand and retract the finger member 12 back into the sleeve just far enough for the wiping blade 22 to be disposed within the proximate end 24 of the sleeve member and between the inwardly extending ribs 28 and 30 on the interior surface of the sleeve member, as best illustrated in FIG. 7. With the wiping blade 22 thus protected, the user may grasp the flared proximate end 26 of the sleeve member 14 with her thumb of the hand carrying the finger member 12, and both members are simultaneously withdrawn. Thus the wiping blade 22 with the cells 40 thereon will not be wiped off against the interior of the vagina or otherwise damaged or contaminated during the process.

After the apparatus 10 has been withdrawn from the vagina, the finger member 12 may be pushed forward to the position illustrated in FIG. 6 and the cervical tissue or cells 40 which have been gathered on the scraping element 22, may be transferred carefully onto a glass slide by gently pressing either side of the resiliently flexible wiping blade to the slide, and then wiping the blade from one side to the other. The slide is then fixed for examination and the apparatus 10 may be discarded. The slide may then be mailed or transported to the clinic or laboratory for cytological, bacteriological, or other examination.

It may be seen that the present invention may be used safely by an untrained individual to obtain cervical tissue and cells for examination, and the entire operation can be done with little or no discomfort and in privacy such as in the user's own home. Since the wiping blade is located on the end of the finger and is of a resilient flexible nature, a gentle wiping action prevents injury or irritation. The apparatus permits women to obtain the benefit of a medical test which otherwise many would forego for reasons of expense or modesty or embarrassment.

The foregoing detailed description of the preferred embodiment has been given by way of example and suitable changes, modifications, or variations may be undertaken without departing from the scope of the invention as defined by the claims:

What is claimed is:

1. A kit having component parts capable of being assembled and inserted into the vagina for the gathering of cervical cell specimens, said kit comprising the combination of an elongated, tubular finger member formed of a thin, elastically resilient material, closed at its distal end and open at its proximate end and adapted to accommodate and resiliently grip a person's finger, said finger member carrying adjacent its distal end a raised wiping element; a tubular sleeve member open at its ends and having an inside dimension larger than the exterior dimension of said finger member and adapted to be fitted over and slidably receive therewithin the distal end and wiping element of said finger member, said sleeve member being shorter in length than said finger member, whereby said sleeve member may shield said finger member distal end and wiping element from contamination contact with the vaginal wall during insertion of said members into and withdrawal from the vagina and after insertion the finger member scraping element may be extended beyond the distal end of said sleeve member to obtain the desired cervical specimens.

2. The apparatus of claim 1 in which the finger member is constructed of an elastomeric material.

3. The apparatus of claim 2 which said sleeve member is constructed of an elastomeric material and is thicker and stiffer than said finger member.

4. The apparatus of claim 1 in which said sleeve member is flared at its proximate end.

5. The apparatus of claim 1 in which said raised wiping element is integral with and of the same material as the rest of said finger member.

6. The apparatus of claim 1 in which said raised wiping element is an elongated longitudinally extending rib protruding from the exterior surface of said finger member.

7. A kit having component parts capable of being assembled and inserted into the vagina for the gathering of cervical cell specimens, said kit comprising the combination of an elongated, tubular finger member formed of an elongated, tubular finger member formed of a thin, elastically resilient material, closed at its distal end and open at its proximate end and adapted to accomodate and resiliently grip a person's finger, said finger member carrying adjacent its distal end a raised wiping element a tubular sleeve member open at its ends and having an inside dimension larger than the exterior dimension of said finger member and adapted to be fitted over and slidably receive therewithin the distal end and wiping element of said finger member and having adjacent its distal end a pair of formations extending inwardly from the interior surface of said sleeve member, said formations being spaced to accommodate therebetween the raised wiping element on said finger member, whereby said sleeve member may shield said finger member distal end and wiping element from contamination contact with the vaginal wall during insertion of said members into and withdrawal from the vagina and after insertion the finger member scraping element may be extended beyond the distal end of said sleeve member to obtain the desired cervical specimens.

8. The apparatus of claim 7 in which said raised wiping element is an elongated longitudinally extending rib-like formation protruding from the exterior surface of said finger member, and said formations extending inwardly from the interior surface of said sleeve member are elongated ribs having a height greater than the wiping element.

* * * * *